United States Patent [19]

Neurath

[11] Patent Number: 4,495,295
[45] Date of Patent: Jan. 22, 1985

[54] IMMUNOASSAYS USING SUPPORT-CONTAINING SEPARATE ANTIGENS AND ANTIBODIES DERIVED FROM AN IMMUNE COMPLEX

[75] Inventor: A. Robert Neurath, New York, N.Y.

[73] Assignee: New York Blood Center, Inc., New York, N.Y.

[21] Appl. No.: 362,718

[22] Filed: Mar. 29, 1982

Related U.S. Application Data

[63] Continuation-in-part of Ser. No. 41,127, May 21, 1979, , and a continuation-in-part of Ser. No. 323,003, Nov. 19, 1981.

[51] Int. Cl.³ ............... G01N 33/54; G01N 33/60
[52] U.S. Cl. ................... 436/518; 436/528; 436/530; 436/531; 436/533; 436/804; 436/807; 436/820; 436/823; 435/4; 435/7
[58] Field of Search ............... 436/518–535, 436/507, 804, 807, 811, 815, 823, 820; 435/4, 7, 5

[56] References Cited

U.S. PATENT DOCUMENTS 3,872,225  3/1975  Coller et al. ..................... 424/1
4,138,213  2/1979  Masson et al. ................. 23/230 B
4,172,117 10/1979  Schober ........................ 436/518
4,210,622  1/1980  Soothill et al. .
4,241,175 12/1980  Miller et al. .

FOREIGN PATENT DOCUMENTS 0019504 11/1980 European Pat. Off .............. 33/56

OTHER PUBLICATIONS

Paganelli, R. et al., Clin. Exp. Immunol., vol. 46, pp. 44–53 (1981).

Primary Examiner—Benjamin R. Padgett
Assistant Examiner—M. Moskowitz
Attorney, Agent, or Firm—Sprung, Horn, Kramer & Woods

[57] ABSTRACT

A process for the detection of an antigen or antibody in a specimen which process comprises:
(a) contacting said specimen with a substrate having bound thereon a mixture of antigens and antibodies to said antigen or antibody in said specimen, said antibodies and said antigens bound to said substrate being separately bound to said substrate and not in the form of an immune complex, incubating the so-contacted substrate and washing the substrate;
(b) contacting the washed material of step 'a' with a radioactive material labeled or enzyme labeled antibody or antigen, incubating the so-contacted material and washing the same; and
(c) effecting radioimmunoassay if said antibody or antigen is radioactive or enzyme labeled immunoassay is said antibody or antigen is enzyme labeled.

26 Claims, No Drawings

IMMUNOASSAYS USING SUPPORT-CONTAINING SEPARATE ANTIGENS AND ANTIBODIES DERIVED FROM AN IMMUNE COMPLEX

BACKGROUND OF THE INVENTION

Cross-reference to Related Application

This is a continuation-in-part of my co-pending application Ser. No. 41,127, filed May 21, 1979 entitled "Labeled Anti-Hapten Antibodies and Their Use as a Universal Reagent for Solid Phase Radio- and/or Enzyme-Immunoassays" the disclosure of which is hereby specifically incorporated herein by reference. This application is also a continuation-in-part of my copending application Ser. No. 323,003 filed Nov. 19, 1981, (NYBC 221) entitled "Sensitive Immunoassays of Antigens or Antibodies Sequestered within Immune Complexes", the disclosure of which is hereby specifically incorporated herein by reference.

Field of the Invention

This invention relates to a process for the detection of an antigen or antibody in a given specimen. More especially, this invention relates to a process for the detection of the presence of an antigen or antibody in a specimen by the use of a universal labeled or enzyme containing antibody or antigen, especially to the use of radioactive labeled or enzyme containing anti-hapten antibodies or antigens in the detection of the presence of and the amount of antigens or antibodies in a test specimen. Still more specifically, this invention relates to a process as described which uses as a source of antibody or antigen that which is obtained by dissociating an immune complex into separate antigen and antibody and disposing separated antigen or antibody on a substrate such as a solid support.

Discussion of Prior Art and Related Applications

Radioimmunoassay techniques for biochemical and immunological studies and for clinical research and diagnosis have become an invaluable tool. However, their applicability has been confined to reasonably well characterized antigens which can be purified and used for the preparation of antisera serving as a source for isolation of immunochemically purified antibodies. Although $^{125}$I-labeled staphylococcal protein A has been suggested as a general radioactive reagent for radioimmunoassay, it cannot be used for sandwich type tests with an antibody-coated solid phase. If neither antigen nor the corresponding antibody are available in relatively purified form, it becomes difficult to prepare radiolabeled reagents for radioimmunoassay (RIA) suitable for the detection of nanogram quantities of antigens.

It therefore became desirable to provide a process for the detection of and the quantitative measurement of antigens, which process could be used for those antibodies and antigens whose purification into relatively purified form was not heretofore known. More especially, it became desirable to provide a process by which nanogram quantities of antigens could be detected, which process did not rely upon the purification of antibodies and antigens as source material for the test. Still more especially, it became desirable to provide a process by which one could use a universal reagent for the detection of the presence of a wide variety of different types of antigens.

In my co-pending application, Ser. No. 41,127, filed May 21, 1979, I described a process for the detection of antigens in a test specimen comprising the steps of (A) contacting a test specimen suspected of containing a given antigen with a substrate coated with antibodies of said antigen, incubating the contacted substrate and washing the substrate;

(B) contacting the washed material of step (A) with a hapten conjugated antibody against said antigen, incubating the so-contacted material and washing the so-incubated material;

(C) contacting the washed material of step (B) with a radioactive material labeled or enzyme labeled antihapten antibody, incubating the so-contacted material and washing the same; and (D) effecting radioimmunoassay if said antibody is radioactive or enzyme labeled immunoassay if said antibody contains an enzyme moiety.

By conducting the process thusly, antigen can be determined without employing a purified source of antigen to prepare purified antibody. Detection of the antigen content in the specimen is effected by comparing the counts derived from the radioimmunoassay or the enzyme concentration in the case of enzyme labeled immunoassay (ELISA) with a standard known to be free of the antigen. Quantitative determination is effected by comparing the counts or enzyme concentration against data derived from the same test protocol using samples of known antigen concentrations.

The procedure of the invention takes advantage of the ability of anti-hapten antibody to readily react with hapten groups on the antibody employed in step (B) which has, in turn, reacted with antigen present in the test specimen. This antigen present in the test specimen has previously reacted with the corresponding antibody held on the substrate. By this technique, the initial antibody employed need not be particularly pure and the quantity of antigen in the specimen is readily detected owing to magnification of test results as a result of the described sandwich technique wherein hapten conjugated groups on the antibody are reacted with anti-hapten antibody. In accordance with that process, the substrate containing the antibody is contacted with test specimens containing the suspected antigen. The suspected antigen reacts with the antibody on the substrate and, in turn, is available for further reaction with the hapten conjugated antibody. When in accordance with step "(B)" of such process, the hapten conjugated antibody contacts the antibody-antigen product resulting from step "(A)", there is formed a sandwich structure wherein the antigen is sandwiched on the one side by the substrate-antibody reagent and on the other side by the hapten conjugated antibody.

The sandwich structure which results, has available hapten groups, since it is the antibody portion of the hapten conjugated antibody that reacts with the antigen held by the substrate-antibody material used in step "(A)". This makes the hapten groups on the hapten conjugated antibody readily available for reaction with radio- or enzyme labeled anti-hapten antibody. Since the hapten conjugated antibody contains multiple hapten moieties, subsequent reaction with the labeled antihapten antibodies provides a substance which provides a magnified count whether analysis be by radioimmunoassay or ELISA. In other words, since the quantity of hapten moieties on the hapten conjugated antibody is higher than the number of antigens adsorbed, a greater number of anti-hapten antibodies will react with those sites. This means that the number of counts per antigen is greater than in the standard radioimmunoassay techniques. This magnification permits the measurement of nanogram quantities of antigen in the test specimen. It is this magnification by the use of hapten conjugated antibody that permits use of antibody reagents in step "(A)" which are not particularly pure.

In my copending application Ser. No. 323,003 filed Nov. 19, 1981, I disclose a process for determining the presence of an antigen or antibody in a sample wherein such antigen or antibody exists in the form of an immune complex which process comprises:

(A) contacting the immune complex originating from the sample with a dissociating buffer whereby said immune complex, if present, is dissociated into antigen and antibody;

(B) contacting a solid support which binds proteins with said dissociating buffer suspected of containing antigen or antibody and removing said buffer;

(C) washing said solid support;

(D) adding protein to fill unoccupied sites on said solid support;

(E) adding radioactively labeled or enzyme labeled antibody or antigen to said solid support, incubating the resultant mass and washing the same;

(F) measuring the radioactivity or enzymatic activity associated with the solid support.

In carrying out the process of Ser. No. 323,003, the process can be performed by isolation of the immune complex from other components with which it is in admixture, normally other proteins. This isolation can involve the removal of immune complexes from sera in which they are present by methods generally known in the art. Accordingly, the immune complexes can be adsorbed onto a solid support or otherwise precipitated from the serum containing the same. This can be effected by precipitation with polyethylene glycol and subsequent adsorption of the immune complex on material such as staphylococci-carrying protein A, by the use of protein A linked to a solid support such as agarose. Alternatively, one can use conglutinin linked to a solid support as adsorbent for the immune complex. After effecting adsorption of the immune complex onto a solid support the serum is removed therefrom, and the solid support is washed to remove excess proteins. There after, whether the antigen and antibody is adsorbed to the solid support, the same is brought in contact with a dissociating buffer which dissociates the immune complex. If the immune complex is one which has been adsorbed to the solid support, not only is the immune complex dissociated into the antibody and antigen components but is also removed from the solid support. To achieve this, dissociating buffers are employed such as urea, guanidine hydrochloride, thiocyanate salts such as sodium and potassium thiocyanate, magnesium chloride, lithium diiodosalicylate or solutions of low (2–3.5) or high (10–11.5) pH. It is important that the buffer be one which substantially completely dissociates the immune complex from the solid support and dissociates the immune complex itself into its component antigen and antibody.

Dissociation of the immune complex is generally carried out at a temperature between 0° and 45° C., preferably room temperature, the dissociating buffer being brought into contact with the immune complex adsorbed on to the solid support for at least two minutes, preferably at least five minutes, and generally between five and 30 minutes. Thereafter, the solid support originally bearing the immune complex is separated from the dissociating buffer which is now suspected of containing antigen or antibody (derived from the immune complex contained in the original sample).

The dissociating buffer suspected of containing antigen or antibody is thereafter brought in contact with the solid support which binds proteins. For this purpose, a wide variety of supports can be used. For instance, one can employ a paper type material which has been treated with a protein binding agent such as diazobenzyloxymethyl paper or diazophenylthioether paper. Treatment of paper with these agents renders the paper capable of binding proteins. Alternatively, one can use a nitrocellulose sheet or similar material. In particular, it is contemplated to use as the solid support a plastic material such as a polystyrene, polyvinyl e.g. polyvinylchloride, polyvinylidene chloride, polyacrylonitrile, polyvinylacetate. Other plastics which can be used include polyethylene, polypropylene, nylon, and derivatized glass.

Quite suprisingly, when these and other protein-adsorbing solid supports are brought in contact with dissociating buffers suspected of containing the antigen or antibody derived from the immune complex, irreversible attachment of the proteins is effected, notwithstanding the copresence of those components in the dissociating buffer which dissociated the antigen antibody and served to remove the antibody from the solid support. In particular, it was quite surprisingly observed that antigen or antibodies in the dissociating buffer attached to a wide variety of solid matrixes and in such environment the presence of the dissociating buffer does not minimize the attachment of the protein to the solid matrixes nor does it cause elution of proteins which had been adsorbed to such matrixes. By effecting adsorbtion of antigen or antibody derived from the immune complex on the solid support, the existence of antibody of antigen can be determined by a simple radioimmunoassay or enzyme labeled immunoassay technique.

SUMMARY OF THE INVENTION

I have now discovered that the product resulting from contact of such solid support which binds proteins with dissociating buffer containing dissociated antigen and antibody can itself be used for various antigen and-/or antibody detection and specifically for the process of my co-pending application Ser. No. 41,127 supra, to bind an antibody or antigen in a test specimen as the antibodies and antigens present on the solid support which binds proteins are each bound directly to the solid support and do not exist in the form of an immune complex. Thus, both the antigens and antibodies are each available to detect the presence of a corresponding antibody or antigen in a specimen.

Broadly, my invention contemplates a process for the detection of an antigen in a specimen which process comprises:

(a) contacting said specimen with a subtrate having bound thereon a mixture of antigens and antibodies to said antigen in said specimen, said antibodies and said antigens bound to said substrate being seperately bound to said substrate and not in the form of an immune complex, incubating the so-contacted substrate and washing the substrate;

(b) contacting the washed material of step 'a' with a radioactive material labeled or enzyme labeled antibody, incubating the so-contacted material and washing the same; and (c) effecting radioimmunoassay if said antibody is radioactive or enzyme labeled immunoassay if said antibody is enzyme labeled.

My invention is also applicable to detection of an antibody in a test specimen using a solid support containing separately adsorbed antigen and antibody (originating from an immune complex) in the detection of an antibody in a test speciman. My invention is carred out by a process which comprises:

(a) contacting said specimen suspected of containing antibody with a substrate having bound thereon a mixture of antibody and antigen to said antibody in said specimen, said antigens and said antibodies bound to said substrate being separately bound to said substrate and not in the form of an immune complex, incubating the so-contacted substrate and washing the substrate;

(b) contacting the washed material of step 'a' with a radioactive material labeled or enzyme labeled antigen, incubating the same and washing the same; and (c) effecting radioimmunoassay if said antigen is radioactive or enzyme labeled immunoassay if said antigen is enzyme labeled.

My invention can also be employed to detect antigens in specimens by competition tests. When used for such purpose, the process of my invention comprises:

(a) contacting a specimen suspected of containing an antigen with a substrate having bound thereon a mixture of antigens and antibodies to said antigen in said specimen, said antibodies and said antigens bound to said substrate being separately bound to said substrate and not in the form of an immune complex, in the presence of a radioactive material labeled or enzyme labeled antigen, incubating the so-contacted substrate and washing the substrate;

(b) comparing the counts if radioimmunoassay is effected or enzymatic activity is enzyme labeled immunoassay is effected with the counts or enzymatic activity of a control carried out without the presence of the specimen. In such case, the presence of antigen is indicated by decreased counts if radioimmunoassay is effected or decreased enzyme activity if enzyme labeled immunoassay is effected.

My invention can further be carried out to determine the presence of antibodies in specimens by competition tests according to which the process is carried out by steps comprising:

(a) contacting said specimen suspected of containing antibody with the substrate having bound thereon a mixture of antibodies and antigens to said antibody in said specimen, said antigens and said antibodies bound to said substrate being separately bound to said substrate and not in the form of an immune complex, in the presence of a radioactive material labeled or enzyme labeled antibody, incubating the so-contacted substrate and washin the substrate;

(b) comparing the counts or enzymatic activity with the counts or enzymatic activity of a control carried out without the use of a specimen. The presence of antibody is indicated by decreased counts or decreased enzyme activity.

DESCRIPTION OF SPECIFIC EMBODIMENTS

Therefore, my invention when applied to the detection of antigen in a specimen in one embodiment comprises:

(A) contacting said specimen with a substrate having bound thereon a mixture of antigens and antibodies to said antigen in said specimen, said antibodies and said antigens bound to said substrate being separately bound to said substrate and not in the form of an immune complex, incubating the so-contacted substrate and washing the substrate;

(B) contacting the washed material of step "(A)" with a hapten-conjugated antibody against said antigen, incubating the so-contacted material and washing the so-contacted material;

(C) contacting the washed material of step "(B)" with a radioactive material labeled or enzyme containing anti-hapten antibody, incubating the so-contacting material and washing the same; and (D) effecting radioimmunoassay if said antibody is radioactive or enzyme labeled immunoassay if said antibody is enzyme labeled.

My invention can also be applied to the detection of the presence of an antibody in a specimen which process comprises:

(A) contacting said specimen suspected of containing an antibody with a substrate having bound thereon a mixture of antibodies and antigens of said antibody in said specimen, said antigens and said antibodies bound to said substrate being separately bound to said substrate and not in the form of an immune complex, incubating the so-contacted substrate and washing the same;

(B) contacting the washed material of step "(A)" with a hapten-conjugated antigen against said antibody, incubating the so-contacted material and washing the so-incubated material;

(C) contacting the washed material of step "(B)" with a radioactive material labeled or enzyme containing antihapten antibody, incubating the so-contacted material and washing the same; and (D) effecting radioimmunoassay if said antibody is radioactive or enzyme labeled immunoassay if said antibody is enzyme labeled.

The heart of my invention lies in the use of a novel material obtained during the immunoassay of my co-pending application Ser. No. 323,003, supra. That material comprises the solid support which binds protein onto which there is separately bound a mixture of antigens and antibodies where the antigens are directly bound to the solid support and the antibodies themselves are directly bound to the solid support and the antigens and antibodies so-bound to the solid support do not exist in the form of an immune complex. This intermediate is therefore useful as the substrate in the process of my co-pending application Ser. No. 41,127, discussed supra.

It is to be understood that the heart of my invention lies in the fact that one can convert an immune complex into a useful diagnostic aid by dissociating that immune complex in a dissociating buffer, whether or not the immune complex has been pre-disposed on a solid support such as Staphylococcoi protein A or the like. That dissociating buffer containing dissociated antigen and antibody can form a valuable diagnostic aid simply by contacting that mixture with a solid support which binds proteins. Following incubation and washing and separation of the so-contacted protein binding support, there is obtained a useful diagnostic agent. Of course, one need not obtain the protein binding solid support - antibody, antigen material as a result of another assay. The heart of the invention resides in the conversion of an immune complex into its component antigen and antibody and the disposition of antigens and antibodies separately from one another, and not in a form of an immune complex, onto a protein binding solid support. Once this is obtained, the resultant reagent can be used in the detection of antigens or antibodies by the procedures described above. Of course, when used in the detection of an antigen, for instance, the antigen which is copresent on the protein-binding support has no special function since the antibody also present thereon is that which binds the antigen of the specimen. The reagent, however, is also useful in the separate detection of antibodies in a specimen where the specimen suspected of containing antibody is brought in contact with the substrate having bound thereon a mixture of antibody and antigen, in which the case the antibody bound to the substrate performs no function. Nevertheless, from one treatment there is obtained a diagnostic reagent which is useful in a number of different assays.

Generally speaking, the protein binding solid support is treated with the dissociating buffer containing antigen and antibody at a temperature between 0° and 45°, preferably between 15° and 25° C. for at least 60 minutes, preferably at least two hours and generally overnight. This insures maximum adsorption of antigen and antibody, separately from one another, onto the protein binding solid support. It should be noted that for this adsorption it is unnecessary that the solid protein binding sorbent be preteated with a protein binding agent. After the protein solid sorbent is treated with the dissociating buffer containing antigen and antibody, the solid support is washed free of extraneous material.

Thereafter, those sites on the solid support not occupied by antigen or antibody are filled with protein so that substantially all of the available sites on the protein binding solid support are occupied. This insures that upon subsequent addition of a test specimen containing antigen or antibody as the case may be, reaction occurs predominantly or only upon the pre-deposited antigen or antibody derived from the dissociating buffer containing composition.

To this end, one can use a wide variety of materials to occupy the unoccupied binding sites on the solid support. These include in particular proteins, notably the following binding site occupiers: bovine serum albumin, gelatine, normal human serum or animal sera (bovine, calf, fetal calf, chicken, etc.). Preferably the solid support is incubated with a solution of bovine serum albumin to saturate the unoccupied protein binding sites.

Thereafter, the sample is washed free of extraneous material, and there is added the test specimens suspected of containing antigen or antibody as the case may be.

The process of the invention can be used with respect to any antigen, the presence of which is suspected in a given serum. All that is required is that an antibody to such suspected antigen be deposited on a substrate, that the specimen containing the suspected antigen contact the antibody on the substrate, incubation is effected and the so-incubated material is washed. Thereafter, in accordance with the second procedural series of steps, the washed material is contacted with hapten conjugated antibody against said antigen, which contacting is also followed by incubation and washing. These steps provide the hapten moieties on the antibody against the suspected antigen, which hapten moieties will react with radioactive labeled or enzyme containing antihapten antibody. Thereafter, the anti-hapten antibody which is either radioactive labeled or contains an enzyme is contacted with the washed material which is followed by incubation and washing. Radioimmunoassay or enzyme labeled immunoassay is effect to determine qualitatively the presence of the antigen and quantitatively the amount of antigen by comparison with prepared standards. The higher the counts from a $\gamma$-counter or higher concentration of enzyme, the higher is the quantity of antigen in the test specimen.

Antigen whose presence and amount can be detected in accordance with the claimed process include essentially any antigen, for example viral, e.g., hepatitis B, influenza, adenovirus, and all other viral antigens, as well as bacterial antigens, tumor-specific antigens, serum antigens, enzyme proteins and all other antigens having at least two antigenic sites.

The antibodies of these antigens can be hapten conjugated with a wide variety of haptens including those which provide the following hapten moieties: dinitrophenyl, trinitrophenyl, diazotized sulfanilic acid, p-azobenzene arsonate, benzyl penicillin, p-azobenzoate, aspirin, fluorescein isothiocyanate, p-iodobenzoate, p-(p'-hydroxyphenylazo) benzoate, phosphorylcholine and others.

The conjugation of haptens with proteins and the preparation of anti-hapten antibodies and their properties have been extensively reviewed (see, for example: "Advanced Immunochemistry", E. D. Day, Williams E. Williams, Baltimore, 1972; A. L. deWeck, "Low Molecular Weight Antigens" in: THE ANTIGENS, Ed. M. Sela, Academic Press, New York, 1974, Volume 2, pages 142-249).

Anti-hapten antibodies can be formed which correspond, in respect of the hapten moiety, to the hapten moiety on the conjugated antibody. Thus, the labeled anti-hapten antibody used in step "(C)" corresponds with respect to its hapten moiety to the hapten moiety of the hapten conjugated antibody against the suspected antigen. The same can be prepared in known manner, as by haptenating an antigen and introducing the so-haptenated antigen into a test animal, such as a rabbit, to effect an antibody response. As a result thereof, as is known, there is formed the antibody to the antigen and an anti-hapten antibody. The resultant serum is recovered and the anti-hapten antibody is separated from the other serum proteins, including the antibody to the original antigen.

The anti-hapten antibody is thereafter labeled, either with a radioactive material such as $I^{125}$ or $I^{131}$ or is conjugated with an enzyme whereby there is formed an enzyme-containing anti-hapten antibody. This enzyme-containing anti-hapten antibody can then be used as a "labeled" anti-hapten antibody—labeled in the sense that it contains an enzyme, but is not radioactive. Detection of the adsorption of the "labeled" anti-hapten antibody can be by RIA or ELISA in accordance with known techniques. RIA involves the use of a radiation detection means, whereas ELISA involves a measurement of the concentration of enzyme. The higher the enzyme concentration, the higher is the concentration of antigen adsorbed and the concentration of antigen in the original test specimen.

The incubation required in acoordance with steps (A), (B), and (C) can be effected in known manner, such as under the following conditions: 1–8 hours t 37°–50° C. and 16–72 hours at 18°–30° C.

Washing is typically effected using an aqueous solution such as one buffered at a pH of 6–8, preferably at a pH of about 7, employing an isotonic saline solution.

The process of the invention is, of course, equally applicable to the detection of the presence of an antibody in a specimen by an analogous procedure wherein the specimen suspected of containing an antibody is brought in contact with the reagent comprising a mixture of antibodies and antigens on a protein-binding substrate followed by incubation and washing. In such instance the so-washed material is thereafter contacted with a hapten-conjugated antigen, incubated and washed. Thereafter, the material so-obtained is brought in contact with the radioactive material labeled or enzyme containing anti-hapten antibody. Following incubation and washing, radio immunoassay or enzyme labeled immunoassay, is effected depending upon whether or not a radioactive or enzyme-containing anti-hapten antibody was employed.

In carrying out the process of the invention, it is preferred that in step "(C)" there be used radioactive material labeled or enzyme containing anti-hapten antibodies which have been obtained by dissociation of an anti-hapten antibody-antigen immune complex. Such anti-hapten antibodies can be prepared by haptenating an antigen and introducing the so-haptenated antigen into a test animal such as a rabbit to effect an antibody response. As a result thereof, there is obtained an immune complex which can be dissociated by use of a dissociating buffer such as one of those listed above and the anti-hapten antibody can be recovered by column chromatography. For instance, anti-DNP can be isolated from anti-DNPBSA (bovine serum albumin) by contacting 2 ml of the anti-serum with 10 mg DNP-apoferritin followed by incubation for one hour at 37° C., overnight at 4° C., and centrifugation for one hour at 90,000 xg. The resultant pellet is dissolved in 1 ml of 8 molar urea-0.01 molar phosphate pH 8.0–0.1% Nonidet P-40 (BDH Chemicals, Ltd., Poole, England) (UPN) and applied to a 2 ml column of DEAE-cellulose prewashed with UPN. Anti-DNP IgG can be recovered from the void volume of the column following elution with UPN.

In order to more fully illustrate the nature of the invention and the manner of practicing the same; the following is presented.

EXAMPLE

Development Of A Test For Antibodies To Hepatitis B Core Antigen [Anti-HB$_c$]

(A) Preparation of [$^{125}$I] labeled Anti-HB$_c$.

Anti-HB$_c$ was isolated from anti-HB$_c$-positive sera by chromatography on DEAE-cellulose (Fudenberg, H.H. (1967) in Methods in Immunology and Immunochemistry, eds. Williams, C.A. & Chase, M.W. (Academic Press, New York), Vol. 1, pp. 307–385.) and labeled with $^{125}$I by one of the standard radiolabeling techniques.

(B) Preparation of Polystyrene Beads Created with HB$_c$Ag originating from an Immune Complex.

Serum containing HBV (hepatitis B virus) was treated for 1 hour at 37° C. with 2-mercaptoethanol (ν100μ/ml) and the detergent Nonidet P-40 (1 mg/ml) to release HB$_c$Ag from HBV particles. Since pratically all sera containing HBV also contain an excess of anti-HB$_c$, HB$_c$Ag-anti-HB$_c$ complexes are formed. These complexes were isolated in the following way:

One part of treated serum was mixed with 9 parts of 0.14 M NaCl-0.01 M Tris pH 7.2 (TS), incubated at 37° C. for 45 min. and centrifuged for 20 min. at 1,700 × g without refrigeration. The supernatant fluids were mixed with an equal volume of ice-cold TS containing 40 g/liter of PEG and 30 g/liter of Tween 20. After standing 90 min. at 0° C., the samples were centrifuged for 20 min. at 1,700 × g (4° C). The precipitates were washed twice with 30 parts each of TS containing 25 g/liter of PEG and 15 g/liter of Tween 20. The final pellets after recentrifugation contained 0.1 to 0.2% of protein originally present in serum. The isolated immune complexes were dissolved in 3 M NaSCN and used for coating of polystyrene beads. After overnight incubation at 20° C., the beads were used for tests.

(C) Performance of Tests.

Specimens (400 ml) of anti-HB$_c$—positive sera and negative controls, respectively, were added to the beads together with a constant amount of $^{125}$I-anti-HB$_c$. The beads were incubated at room temperature, preferably overnight, washed with Tris-buffered saline and countered in a γ counter.

Test results:

negative control=A cmp positive control=B cpm where A>B (since unlabeled anti-HBc competes with $^{125}$I-anti-HB$_c$ for the same sites on HB$_c$A$_g$-coated beads)

All specimens for which cpm $\leq$A/2 are considered positive. For titration of anti-HB$_c$ in a specimen, the latter is serially diluted in normal human serum and tested. The highest dilution for which cpm $\leq$A/2 corresponds to the endpoint titer.

What is claimed is:

1. A process for the detection of an antigen in a specimen which process comprises:

(a) contacting said specimen with a substrate having bound thereon a mixture of antigens and antibodies to said antigen in said specimen, said antibodies and said antigens bound to said substrate being separately bound to said substrate and not in the form of an immune complex, incubating the so-contacted substrate and washing the substrate;

(b) contacting the washed material of step 'a' with a radioactive material labeled or enzyme labeled antibody, incubating the so-contacted material and washing the same; and (c) effecting radioimmunoassay if said antibody is radioactive or enzyme labeled immunoassay is said antibody is enzyme labeled.

2. A process according to claim 1, wherein the washed material of step 'a' is contacted with a hapten conjugated antibody against said antigen of said specimen, the so-contacted material is incubated and washed and thereafter the resultant washed material is contacted with a radioactive material labeled or enzyme labeled anit-hapten antibody, incubated and washed and radioimmunoassay is effected if said anti-hapten antibody is radio labeled or enzyme labeled immunoassay is effected if said anti-hapten antibody is enzyme labeled.

3. A process according to claim 1, wherein said substrate having bound thereon a mixture of antigens and antibodies is a protein binding solid support in which the sites free of antigen or antibody are substantially filled with a protein binding site occupier.

4. A process according to claim 3, wherein said protein site occupier is bovine serum albumin, gelatin, a normal human serum or an animal serum.

5. A process according to claim 3, wherein said protein binding solid support is derivatized paper or plastic material.

6. A process according to claim 3, wherein said solid support is a paper derivative.

7. A process according to claim 6, wherein said paper is a nitrocellulose paper.

8. A process according to claim 6, wherein said paper is a diazobenzyloxymethyl paper or a diazophenylthioether paper.

9. A process according to claim 3, wherein said solid support is a plastic material.

10. A process according to claim 3, wherein said solid support comprises polystyrene.

11. A process according to claim 3, wherein said solid support comprises a polyvinyl material.

12. A process according to claim 3, wherein said solid support comprises a polyolefin.

13. A process for detecting the presence of an antigen in a specimen which comprises:
   (a) contacting the specimen suspected of containing an antigen with a substrate having bound thereon a mixture of antigens and antibodies to said antigen in said specimen, said antibodies and said antigen being bound to said substrate separately not being in the form of an immune complex, in the presence of a radioactive material labeled or enzyme labeled antigen, incubating the so-contacted substrate and washing the substrate;
   (b) effecting radioimmunoassay if said antigen is radioactive or enzyme labeled immunoassay if said antigen is enzyme labeled; and
   (c) comparing the counts if radioimmunoassay is effected or enzymatic activity if enzyme immunoassay is effected with the counts or enzymatic activity of a control carried out without the presence of said specimen.

14. A process for the detection of the presence of an antibody in a test specimen which process comprises:
   (a) contacting said specimen suspected of containing antibody with a substrate having bound thereon a mixture of antibody and antigen to said antibody in said specimen, said antigens and said antibodies bound to said substrate being separately bound to said substrate and not in the form of an immune complex, incubating the so-contacted substrate and washing the substrate;
   (b) contacting the washed material of step 'a' with a radioactive material labeled or enzyme labeled antigen, incubating the same and washing the same; and
   (c) effecting radioimmunoasssay if said antigen is radioactive or enzyme labeled immunoassay if said antigen is enzyme labeled.

15. A process according to claim 14, wherein following step 'a', the washed material of step 'a' is contacted with a hapten conjugated antigen against said antibody, the so-contacted material is incubated and washed and the resultant washed material is contacted with a radioactive material labeled or enzyme-containing anti-hapten antibody incubated and washed after which radioimmunoassay is effected if said antibody is radio active or enzyme labeled immunoassay is effected if said antibody is enzyme labeled.

16. A process according to claim 14, wherein said substrate comprises a protein binding solid support whose protein binding sites not occupied by antigen or antibody are substantially filled with a protein binding site occupier.

17. A process according to claim 16, wherein said protein site occupier is bovine serum albumin, gelatin, a normal human serum or an animal serum.

18. A process according to claim 16, wherein said protein binding solid support is derivatized paper or plastic material.

19. A process according to claim 18, wherein said solid support is a paper (cellulose) derivative.

20. A process according to claim 18, wherein said support is nitrocellulose paper.

21. A process according to claim 18, wherein said solid support is a diazobenzyloxymethyl paper or a diazophenylthioether paper.

22. A process according to claim 18, wherein said solid support comprises a plastic material.

23. A process according to claim 18, wherein said solid support comprises a polyvinyl material.

24. A process according to claim 18, wherein said support comprises a polystyrene.

25. A process according to claim 18, wherein said support comprises a polyolefin.

26. A process for the detection of the presence of an antibody in a specimen which process comprises:
   (a) contacting said specimen suspected of containing antibody with a substrate having bound thereon a mixture of antibodies and antigens to said antibody in said specimen, said antigen and said antibodies bound to said substrate being seperately bound to said substrate and not in the form of an immune complex, in the presence of a radioactive material labeled or enzyme labeled antibody, incubating the so-contacted substrate and washing the substrate;
   (b) comparing the counts or enzymatic activity with the counts or enzymatic activity of a control carried out without the use of said specimen.

* * * * *

UNITED STATES PATENT AND TRADEMARK OFFICE
CERTIFICATE OF CORRECTION

PATENT NO. : 4,495,295

DATED : January 22, 1985

INVENTOR(S) : A. Robert Neurath

It is certified that error appears in the above-identified patent and that said Letters Patent is hereby corrected as shown below:

| | |
|---|---|
| Col. 3, line 48 | Correct "Thereafter" |
| Col. 4, line 30 | After "antigen" insert --from the-- |
| Col. 4, line 41 | Before "antigen" delete "of" and substitute --or-- |
| Col. 5, line 13 | Correct spelling of "specimen" |
| Col. 5, line 63 | Correct spelling of "washing" |
| Col. 7, line 33 | Correct spelling of "pretreated" |
| Col. 8, line 8 | Correct "effect" to --effected-- |
| Col. 9, line 67 | Correct spelling of "practically" |
| Col. 10, line 20 | After "400" delete "ml" and substitute --µl-- |
| Col. 10, lines 32 and 35 | Delete " $\leqq$ " and substitute -- $\leq$ -- |
| Col. 10, line 52 | After "immunoassay" delete "is" and substitute --if-- |
| Col. 12, line 1 | Correct spelling of "radio immunoassay" |
| Col. 12, lines 11, 12 | Correct "radioactive" |

Signed and Sealed this

Seventeenth Day of September 1985

[SEAL]

Attest:

DONALD J. QUIGG

Attesting Officer

Commissioner of Patents and Trademarks—Designate